United States Patent [19]

Gray et al.

[11] Patent Number: 5,288,622

[45] Date of Patent: * Feb. 22, 1994

[54] HUMAN NERVE GROWTH FACTOR BY RECOMBINANT TECHNOLOGY

[75] Inventors: Alane M. Gray; Axel Ullrich, both of San Francisco, Calif.

[73] Assignee: Genentech, Inc., South San Francisco, Calif.

[ * ] Notice: The portion of the term of this patent subsequent to Dec. 8, 2009 has been disclaimed.

[21] Appl. No.: 897,221

[22] Filed: Jun. 11, 1992

Related U.S. Application Data

[60] Continuation of Ser. No. 242,093, Sep. 8, 1988, Pat. No. 5,169,762, which is a division of Ser. No. 471,962, Mar. 3, 1983, abandoned.

[51] Int. Cl.$^5$ .................... C12P 21/06; C12P 21/02; A61K 37/36; C07K 13/00
[52] U.S. Cl. .................... 435/69.4; 530/399; 536/23.51; 536/23.5; 435/320.1; 435/70.1; 435/71.1
[58] Field of Search .................... 435/69.4, 172.3; 935/11, 22, 52; 530/399

*Primary Examiner*—Robert J. Hill, Jr.
*Assistant Examiner*—K. Cochrane Carlson
*Attorney, Agent, or Firm*—Sean A. Johnston

[57] ABSTRACT

The β-subunit of human nerve growth factor (βNGF) is prepared in essentially pure form in commercially viable quantities using recombinant DNA technology. The nucleotide sequence and vectors encoding human βNGF and host cells transformed with the vectors are also provided.

9 Claims, 14 Drawing Sheets

MOUSE βNGF SEQUENCES

```
     1                                          10
     Ser Ser Thr His Pro Val Phe His Met Gly Glu Phe Ser Val Cys
     TCG TCG ACG CAT CCG GTG TTT CAT ATG GGG GAA TTT TCG GTG TGT
5'    A   A   A      C   A   C       C       A   G  C   A   A   C
     AGT AGT  T       T   T                               AGT  T
      C   C   C       C   C                                C   C

20
     Asp Ser Val Ser Val Trp Val Gly Asp Lys Thr Thr Ala Thr Asn
     GAT TCG GTG TCG GTG TGG GTG GGG GAT AAA ACG ACG GCG ACG AAT
      C   A   A   A   A           A   C   G   A   A   A   A   C
         AGT  T  AGT  T                       T   T   T   T
          C   C   C   C                       C   C   C   C

40
     Ile Lys Gly Lys Glu Val Thr Val Leu Ala Glu Val Asn Ile Asn
     ATT AAA GGG AAA GAA GTG ACG GTG CTG GCG GAA GTG AAT ATT AAT
      C   G   A   G   G   A   A   A   A   T   A   G   C   C   C
      A       T   C   C   T   T   T   T   C   T   C        C   A
                  C   C   C   C   C   C   C   C        C 50                                 60
     Asn Ser Val Phe Arg Gln Tyr Phe Phe Glu Thr Lys Cys Arg Ala
     AAT TCG GTG TTT CGG CTA TAT TTT TTT GAA ACG AAA TGT CGG GCG
      C   A   A       C   A       C   C   G   A   G   C   A   A
         AGT  T       A               C       T           T   T
          C   C       T                       C           C   C
```

3  | 3' ATA AAA AAA CTT TG 5'
       G   G   G    C
          16 x 14

Fig. 1A.

```
                                              70
Ser Asn Pro Val Glu Ser Gly Cys Arg Gly Ile Asp Ser Lys His
TCG AAT CCG GTG GAG TCG GGG TGT CGG GGG ATT GAT TCG AAA CAT
 A       C   A   A   A   A   A   C   A   C   C   A   G   C
AGT          T           AGT     T       A       AGT
 C           C            C       C               C
```

```
                                                  2 │ 3' TTT GTA │
                                                    │     C   G  │
                                                    │    8 x 12  │
```

```
                            80                                     90
Trp Asn Ser Tyr Cys Thr Thr Thr His Thr Phe Val Lys Ala Leu
TGG AAT TCG TAT TGT ACG ACG ACG CAT ACG TTT GTG AAA GCG CTG
     C   A   C   C   A   A   A   C   A   C       G   A   A
        AGT                  T   T   T   T           T   T
         C                   C   C   C   C           C   C
```

```
│ ACC TTA 5' │
│      G     │
│  8 x 12    │
```

```
                                              100
Thr Thr Asp Glu Lys Gln Ala Ala Tyr Arg Phe Ile Arg Ile Asn
ACG ACG GAT GAA AAA CAA GCG GCG TAT CGG TTT ATT CGG ATT AAT
 A   A   C   G   G   G   A   A   C   A   C   C   A   C   C
 T   T           G       T   T       A       A   A       A
 C   C                   C   C                   C
```

```
1 │ 3' CTA CTT TTT GTT CG 5' │
  │     G   C   C   C        │
  │        16 x 14           │
```

```
                    110                              118
Thr Ala Cys Val Cys Val Leu Ser Arg Lys Ala Thr Arg
ACG GCG TGT GTG TGT GTG CTG TCG CGG AAA GCG ACG CGG         3'
 A   A   C   A   C   A   A   A   A   G   A   A   A
 T   T       T       T   T  AGT  A       T   T   T
 C   C       C       C   C   C   C       C   C   C
```

*Fig. 1B.*

```
AGCGCATCGAGTGACTTTGGAGCTGGCCTTATATTTGGATCTCCCGGGCAGCTTTTTGG
1         10        20        30        40        50
```

```
                          -187                                -180
                          met  leu cys leu lys pro val lys leu gly ser
AAACTCCTAGTGAAC           ATG  CTG TGC CTC AAG CCA GTG AAA TTA GGC TCC
60             70              80              90              100
```

```
                       -170
leu glu val gly his gly gln his gly gly val leu ala cys gly
CTG GAG GTG GGA CAC GGG CAG CAT GGT GGA GTT TTG GCC TGT GGT
            110             120             130             140             150
```

```
    -160                                        -150
arg ala val gln gly ala gly trp his ala gly pro lys leu thr
CGT GCA GTC CAG GGG GCT GGA TGG CAT GCT GGA CCC AAG CTC ACC
            160             170             180             190
```

```
                       -140
ser val ser gly pro asn lys gly phe ala lys asp ala ala phe
TCA GTG TCT GGG CCC AAT AAA GGT TTT GCC AAG GAC GCA GCT TTC
            200             210             220             230             240
```

```
    -130                                            -120
tyr thr gly arg ser glu val his ser val met ser met leu phe
TAT ACT GGC CGC AGT GAG GTG CAT AGC GTA ATG TCC ATG TTG TTC
            250             260             270             280
```

```
                       -110
tyr thr leu ile thr ala phe leu ile gly val gln ala glu pro
TAC ACT CTG ATC ACT GCG TTT TTG ATC GGC GTA CAG GCA GAA CCG
            290             300             310             320             330
```

```
    -100                                         -90
tyr thr asp ser asn val pro glu gly asp ser val pro glu ala
TAC ACA GAT AGC AAT GTC CCA GAA GGA GAC TCT GTC CCT GAA GCC
            340             350             360             370
```

```
                                -80
his trp thr lys leu gln his ser leu asp thr ala leu arg arg
CAC TGG ACT AAA CTT CAG CAT TCC CTT GAC ACA GCC CTC CGC AGA
            380             390             400             410             420
```

```
    -70                                          -60
ala arg ser ala pro thr ala pro ile ala ala arg val thr gly
GCC CGC AGT GCC CCT ACT GCA CCA ATA GCT GCC CGA GTG ACA GGG
            430             440             450             460
```

```
                         -50
gln thr arg asn ile thr val asp pro arg leu phe lys lys arg
CAG ACC CGC AAC ATC ACT GTA GAC CCC AGA CTG TTT AAG AAA CGG
            470             480             490             500             510
```

```
    -40                                          -30
arg leu his ser pro arg val leu phe ser thr gln pro pro pro
AGA CTC CAC TCA CCC CGT GTG CTG TTC AGC ACC CAG CCT CCA CCC
            520             530             540             550
```

*Fig. 4A.*

```
                              -20
         thr ser ser asp thr leu asp leu asp phe gln ala his gly thr
         ACC TCT TCA GAC ACT CTG GAT CTA GAC TTC CAG GCC CAT GGT ACA
         560         570         580         590         600

-10      ▨▨▨▨▨
         ile pro phe asn arg thr his arg ser lys arg │ser ser thr his
         ATC CCT TTC AAC AGG ACT CAC CGG AGC AAG CGC │TCA TCC ACC CAC
                 610         620         630             640

10
         pro val phe his met gly glu phe ser val cys asp ser val ser
         CCA GTC TTC CAC ATG GGG GAG TTC TCA GTG TGT GAC AGT GTC AGT
         650         660         670         680         690

20                                  30
         val trp val gly asp lys thr thr ala thr asp ile lys gly lys
         GTG TGG GTT GGA GAT AAG ACC ACA GCC ACA GAC ATC AAG GGC AAG
                 700         710         720         730

40                       ▨▨▨▨▨
         glu val thr val leu ala glu val asn ile asn asn ser val phe
         GAG GTG ACA GTG CTG GCC GAG GTG AAC ATT AAC AAC AGT GTA TTC
         740         750         760         770         780

50                                  60
         arg gln tyr phe phe glu thr lys cys arg ala ser asn pro val
         AGA CAG TAC TTT TTT GAG ACC AAG TGC CGA GCC TCC AAT CCT GTT
                 790         800         810         820

70
         glu ser gly cys arg gly ile asp ser lys his trp asn ser tyr
         GAG AGT GGG TGC CGG GGC ATC GAC TCC AAA CAC TGG AAC TCA TAC
         830         840         850         860         870

80                                  90
         cys thr thr thr his thr phe val lys ala leu thr thr asp glu
         TGC ACC ACG ACT CAC ACC TTC GTC AAG GCG TTG ACA ACA GAT GAG
                 880         890         900         910

100
         lys gln ala ala trp arg phe ile arg ile asp thr ala cys val
         AAG CAG GCT GCT TGG AGG TTC ATC CGG ATA GAC ACA GCC TGT GTG
         920         930         940         950         960

110                            ▬▬▬▬▬
         cys val leu ser arg lys ala thr arg│arg gly OP
         TGT GTG CTC AGC AGG AAG GCT ACA AGA│AGA GGC TGA CTTGCCTGCAGC
                 970         980             990         1000        1010

CCCCTTCCCCACCTGCCCCCTCCACATCTCCTGGGCCCCTCCCTACCTCAGCCTGTAAATTA
                 1020        1030        1040        1050        1060        1070

TTTTAAATTATAAGGACTGCATGATAATTTATCGTTTATACAATTTTAAAGACATTA
                 1080        1090        1100        1110        1120        1130

TTTATTAAATTTTCAAAGCATCCTGTATACCGAA
                 1140        1150        1160
```

```
AGCGCATCGAGTGACTTTGGAGCTGGCCTTATATTTGGATCTCCCGGGCAGCTTTTTGGA
```

```
                            -187                          -180
                            met leu cys leu lys pro val lys leu gly ser
AACTCCTAGTGAAC              ATG CTG TGC CTC AAG CCA GTG AAA TTA GGC TCC   m
                            ___ ___ ___ ___ ___ ___ ___ ___ ___ ___ ___  h
```

```
                              -170
leu glu val gly his gly gln his gly gly val leu ala cys  gly
CTG GAG GTG GGA CAC GGG CAG CAT GGT GGA GTT TTG GCC TGT  GGT
___ ___ ___ ___ ___ ___ ___ ___ ___ ___ ___ ___ ___  A   ___
                                         ↑          ser
                                        IVS    -150
  -160
arg ala val gln gly ala gly trp his ala gly pro lys leu thr
CGT GCA GTC CAG GGG GCT GGA TGG CAT GCT GGA CCC AAG CTC ACC    m
         A                                                G
                                                         ser   h
```

```
                       -140
ser val  ser gly pro asn lys gly phe ala  lys asp  ala ala phe
TCA GTG  TCT GGG CCC AAT AAA GGT TTT GCC  AAG GAC  GCA GCT TTC
     C            C       A   C   A        A   GA
    ala                  asn ser          thr  gly
```

```
  -130                                        -120
tyr thr  gly arg ser glu val his ser val met ser met leu phe
TAT ACT  GGC CGC AGT GAG GTG CAT AGC GTA ATG TCC ATG TTG TTC   m
     C        A   C   ↑                                        h
    pro      his thr IVS
```

```
              -110
tyr thr leu ile thr ala phe leu ile gly val  gln ala glu pro
TAC ACT CTG ATC ACT GCG TTT TTG ATC GGC GTA  CAG GCA GAA CCG
                     T   C                    G           A
                                         ile
```

```
  -100                                 -90
tyr thr asp  ser asn val pro glu  gly asp ser val  pro glu ala
TAC ACA GAT  AGC AAT GTC CCA GAA  GGA GAC TCT GTC  CCT GAA GCC   m
 C   T   G            T    C         C   A   A     C   C   T    h
his ser glu               ala        his thr ile      gln val
```

```
                   -80
his trp thr lys leu gln his ser leu asp thr ala leu arg arg
CAC TGG ACT AAA CTT CAG CAT TCC CTT GAC ACA GCC CTC CGC AGA
                                         T       T
```

```
 -70                                      -60
ala arg ser ala pro thr ala pro ile ala ala arg val thr gly
GCC CGC AGT GCC CCT ACT GCA CCA ATA GCT GCC CGA GTG ACA GGG   m
             C       G       G       G           A   G  G    h
                    ala      ala                         ala
```

```
              -50
gln thr arg asn ile thr val asp pro arg leu phe lys lys arg
CAG ACC CGC AAC ATC ACT GTA GAC CCC AGA CTG TTT AAG AAA CGG
                 T       G       G           A   G
```

```
 -40                                          -30
arg leu his ser pro arg val leu phe ser thr gln pro pro pro
AGA CTC CAC TCA CCC CGT GTG CTG TTC AGC ACC CAG CCT CCA CCC   m
     C   GT                          T                   GT   h
        arg                                             arg
```

```
          70
|[glu] ser gly cys arg gly ile asp ser lys his trp asn ser tyr |
| GAG  AGT GGG TGC CGG GGC ATC GAC TCC AAA CAC TGG AAC TCA TAC |
|  C    C                  T       A   G                   T  |
|[asp]                                                          |
|                                                                90
| 80                                                                  |
| cys thr thr thr his thr phe val lys ala leu thr [thr] asp [glu]|
| TGC ACC ACG ACT CAC ACC TTC GTC AAG GCG TTG ACA  ACA  GAT  GAG | m
|  T                       T                   C   TG         GC| h
|                                                 [met]       [gly]|
|                100                                                  |
| lys gln ala ala trp arg phe ile arg ile asp thr ala cys val |
| AAG CAG GCT GCT TGG AGG TTC ATC CGG ATA GAC ACA GCC TGT GTG |
|          C      C   T                    T   G              |
| 110                                                            
| cys val leu ser arg lys ala [thr] arg arg [gly] OP             |
| TGT GTG CTC AGC AGG AAG GCT  ACA  AGA AGA  GGC  TGA CTTGCCTGCAGC | m
|                              GTG            C       CCTGCCGACACG | h
|                             [val]          [ala]
```

```
CCCCTTCCCCACCTGCCCCCTCCACACTCTCCTGGGCCCCTCCCTACCTCAGCCTGTAAA     m
CTCCCTCCCCCTGCCCCCTTCTACACTCTCCTGGGCCCCTCCCTACCTCAACCTGTAAATT   h

TTATTTTAAATTATAAGGACTGCATGATAATTTATCGTTTATACAATTTTAAAGACATTA    m
ATTTTAAATTATAAGGACTGCATGGTAATTTATAGTTTATACAGTTTTAAAGAATCATTA    h

TTTATTAAATTTTCAAAGCATCCTGTATACCGAA                              m
TTTATTAAATTTTTGGAAGCATCCTGTGTGCTGA                              h
```

*Fig. 6C*

Human βNGF Expresssion

```
                                                   EcoRI
         I              II                III               IV
Xbal    MetSerSerHisProIlePheSerSerHisArgGlyGluPheSerValCysAspSerValSerValTrpValGlyAspLysThrAlaT
        ATGTCATGAGTCATCCGATCTTCCACAGGGGCGAATTCTCAGTGTGTGACAGTGTCAGCGTGTGGGTTGGGGATAAGACCACGCCA
CTAGAATT TACAGTAGCTCAGTAGGCTAGAAGGTGTCCCCGCTTAAGAGTCACACACTGTCACAGTCGCACACCCTATTCTGGTGGCGGT
TTAA                                III hrAspIleLysGlyLysGluValMetValLeuGlyGluValAlaAsnIleAsnAsnSerValPheLysGlnTyrPhePheGluThrLysCysArgAspProAs
CAGACATCAAGGGCAAGGAGGTGATGGTGTTGGGAGAGGTGAACATTAACAACAGTGTATTCAAACAGTACTTTTTGAGACAAGTGCGGGACCCAAA
GTCTGTAGTTCCCGTTCCTCCACTACCACAACCCTCTCCACTTGTAATTGTTGTCACATAAGTTTGTCATGAAAAAACTCTGGTTCACGGCCCTGGGTTT nProValAspSerGlyCysArgGlyIleAspSerLysHisTrpAsnSerTyrCysThrThrThrHisThrPheValLysAlaLeuThrMetAspGlyLys
TCCCGGTTGACAGCGGGTGCGGGCATTGACTCAAAGCACTGGAACTCATATTGTACCACGACTCACACCTTTGTCAAGGCGCTGACCATGGATGGCAAG
AGGGCAACTGTCGCCCACGCCCGTAACTGAGTTTCGTGACTTGAGTATAACATGGTGCTGAGTGTGGAAACAGTTCCGCGACTGGTACCTACCGTTC V
GlnAlaAlaTrpArgPheIleArgIleAspThrAlaCysValCysValLeuSerArgLysAlaValAlaValArgEnd
CAGGCTGCCTGGCGCTTTATCCGGATAGATACGGCCTGTGTGTGTCTCAGCAGGAAGGCTGTGAGATAGTCGAC
GTCCGACGGACCGCGAAATAGGCCTATCTATGCCGGACACACACAGAGTCGTCCTTCCGACACTCTATCAGCTG
                        HgiAI                     VI
```

Fig. 7.

HUMAN NERVE GROWTH FACTOR BY RECOMBINANT TECHNOLOGY

This application is a continuation application based on application Ser. No. 07/242,093, filed Sep. 8, 1988 (now U.S. Pat. No. 5,169,762), which is a divisional of application Ser. No. 06/471,962, filed Mar. 3, 1983 (now abandoned).

FIELD OF THE INVENTION

This invention relates to the polypeptide hormone human Nerve Growth Factor (NGF), its preparation using recombinant technology and compositions which contain it.

BACKGROUND OF THE INVENTION

A. Nerve Growth Factor

A multi-component protein of molecular weight ~130,000 has been isolated from mouse salivary glands, it being particularly concentrated in the glands of male mice, which is commonly referred to as "Nerve Growth Factor." The principal neural activity exhibited by the protein has been its ability to cause an increase in the size of sensory neurons, nerve cells which transmit impulses from *sensory* receptors to the brain, and in the size of *sympathetic* neurons, one of the two kinds of neurons which make up the autonomic nervous system which regulates the functional activity of the circulatory system, the glands, smooth muscles and other organs.

NGF as obtained by extraction at neutral pH from mouse salivary glands is known as 7S NGF and is made up of three subunits termed $\alpha$, $\beta$, $\gamma$ subunits. All of the neural activity of 7S NGF is exhibited by the $\beta$ subunit, a dimer of two identical 118 amino acid peptides bound together by non-covalent forces. This subunit is also referred to as 2.5S NGF. The $\alpha$- subunit has no known biological activity. The $\gamma$-subunit, however, is an arginine esteropeptidase. The initial genetic product in the synthesis of NGF is a prepro-NGF polypeptide which is cleaved by the $\gamma$-subunit. The $\gamma$-subunit has also been shown to accelerate wound healing in mice.

Recently, a third NGF component (M. wt. ~116,000) has been reported to have been isolated from mouse salivary glands and to have shown to exhibit the property of being a plasminogen activator, i.e., it converts plasminogen to plasmin, suggesting its utility in the lysis of blood clots. See European Patent Application "Nerve Growth Factor and Process For Obtaining It" 78300656.2 (Publication No. 0002139A1) filed Nov. 22, 1978, published May 30, 1979.

As indicated above, the neural activity of NGF is exhibited by the $\beta$-subunit (hereinafter $\beta$NGF). It has been shown to stimulate markedly regenerative resprouting of transected axons of central adrenergic neurons, a property which makes it useful in the repair of damaged axons.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes and cell cultures. The general means and methods are in hand for the in vitro ligation of various blunt ended or "sticky" ended fragments of DNA, producing potent expression vectors useful in transforming particular organisms, thus directing their efficient synthesis of desired exogenous product. However, on an individual product basis, the pathway remains tortuous and the science has not advanced to a stage where regular predictions of success can be made. Indeed, those who portend successful results without the underlying experimental basis, do so at considerable risk of inoperability.

DNA recombination of the essential elements, i.e., an origin of replication, one or more phenotypic selection characteristics, an expression promoter, heterologous gene insert and remainder vector, generally is performed outside the host cell. The resulting recombinant replicable expression vector, or plasmid, is introduced into cells by transformation and large quantities of the recombinant vehicle are obtained by growing the transformant. Where the gene is properly inserted with reference to portions which govern the transcription and translation of the encoded DNA message, the resulting expression vector is useful to produce the polypeptide sequence for which the inserted gene codes, a process referred to as "expression." The resulting product may be obtained by lysis, if necessary, of the host cell and recovery of the product by appropriate purifications from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment.

Similarly, the art of cell or tissue cultures for studying genetics and cell physiology is well established. Means and methods are in hand for maintaining permanent cell lines, prepared by successive serial transfers from isolated normal cells. For use in research, such cell lines are maintained on a solid support in liquid medium, or by growth in suspension containing support nutriments. Scale-up for large preparations seems to pose only mechanical problems.

Likewise, protein biochemistry is a useful, indeed necessary, adjunct in biotechnology. Cells producing the desired protein also produce hundreds of other proteins, endogenous products of the cell's metabolism. These contaminating proteins, as well as other compounds, if not removed from the desired protein, could prove toxic if administered to an animal or human in the course of therapeutic treatment with desired protein Hence, the techniques of protein biochemistry come to bear, allowing the design of separation procedures suitable for the particular system under consideration and providing a homogeneous product safe for intended use. Protein biochemistry also proves the identity of the desired product, characterizing it and ensuring that the cells have produced it faithfully with no alterations or mutations. This branch of science is also involved in the design of bioassays, stability studies and other procedures necessary to apply before successful clinical studies and marketing can take place.

SUMMARY OF THE INVENTION

The present invention provides the $\beta$-subunit of human NGF, which previously had not been isolated by extraction techniques or otherwise synthesized, in essentially pure form. Further, we have discovered that, unexpectedly, β-NGF can be expressed as a heterologous protein in *E. coli* as a mature polypeptide, i.e., free of any fused homologous protein which might be required to afford it protection from cellular enzymes which recognize it as foreign protein. We believe the β-subunit of NGF to be the smallest protein directly expressed as mature protein in *E. coli*.

The β-NGF which the invention provides is useful in treating nerve damage or for other related purposes for which it is beneficial. Being identical with naturally secreted human β-NGF, but free of other protein of mammalian origin, it is unlikely its use will result in an immunogenic response during treatment with it, unlike the case when peptide hormones of non-human origin are used to treat human illness. Furthermore, being obtained as a heterologous protein, the β-NGF will be essentially free of other proteins of mammalian origin which accompany β-NGF obtained as a tissue extract and which may exhibit undesirable biological activity in compositions which contain them.

The invention is further directed to replicable DNA expression vectors which contain a gene sequence which codes for the polypeptide in expressible form. The invention is also directed to recombinant host cells such as microorganism strains or cell lines transformed with such vectors, and to the cultures thereof. Still further, the invention is directed to compositions comprising the polypeptide for parenteral administration.

Accordingly an object of this invention is to acquire human β-NGF essentially free of other mammalian proteins.

Another object is to obtain human β-NGF in quantities in excess of those which are possible by extraction from natural sources.

BRIEF DESCRIPTION OF THE DRAWINGS

FIGS. 1A and 1B show the amino acid sequence of the β-subunit of mouse NGF and gene sequences coding for it and the complementary DNA strands for specific segments of the gene.

FIGS. 4A and 4B show the physical map of the recombinant phage λhN8 and flanking regions in the human genome.

FIGS. 5A, 5B and 5C show the nucleotide sequence of the human βNGF chromosomal gene.

FIGS. 6A, 6B, and 6C show a comparison of nucleotide sequences of human and mouse Prepro-βNGF gene and amino acid sequences.

FIG. 7 shows the gene constructed for expression of human βNGF.

DETAILED DESCRIPTION

A. Host Cell Cultures and Vectors

Figure 2:
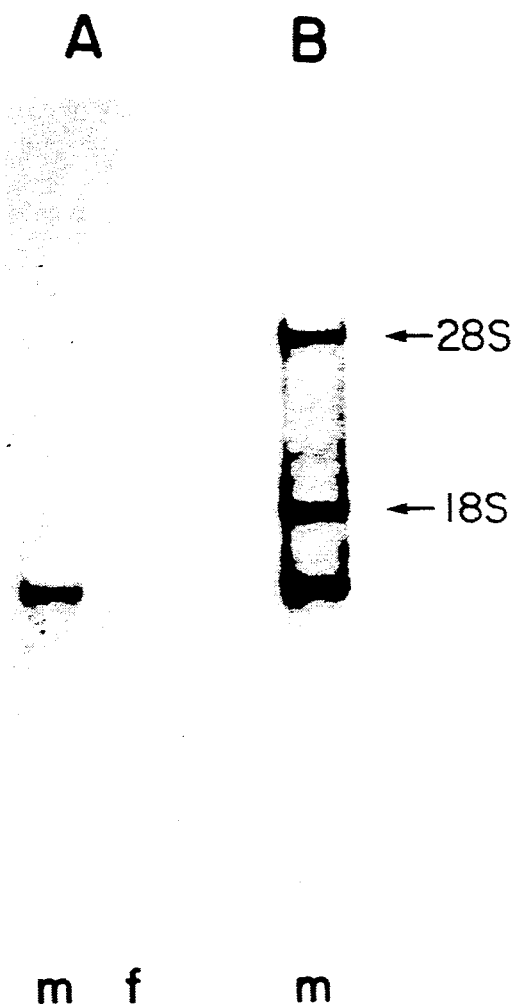
FIGS. 2A and 2B show a Northern Blot Analysis of clones containing segments of βNGF mRNA.

As used in the present application, the term "expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Further as used herein, the term "recombinant host cells" refers to cells which have been transformed with vectors constructed using recombinant DNA techniques.

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, *E. coli* K12 strain 294 (ATTC No. 31446) is particularly useful. Other microbial strains which may be used include *E. coli* strains such as *E. coli* B and *E. coli* X1776 (ATTC No. 31537). These examples are, of course, intended to be illustrative rather than limiting.

Prokaryotes may also be used for expression. The aforementioned strains, as well as *E. coli* W3110 (F⁻, λ⁻, prototrophic, ATTC No. 27325), bacilli such as *Bacillus subtilus*, and other enterobacteriaceae such as *Salmonella typhimurium* or *Serratia marcescens*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar, et al., *Gene* 2:95 (1977)). pBR322 contains genes for ampicillin and tetracycline resistance and thus provides easy means for identifying transformed cells. The pBR322 plasmid, or other microbial plasmid, must also contain, or be modified to contain, promoters which can be used by the microbial organism for expression of its own proteins. Those promoters most commonly used in recombinant DNA construction include the β-lactamase (penicillinase) and lactose promoter systems (Chang et al, *Nature*, 275:615 (1978); Itakura, et al, *Science*, 198: 1056 (1977); Goeddel, et al, *Nature*, 281: 544 (1979)) and a tryptophan (trp) promoter system (Goeddel, et al, *Nucleic Acids Res.*, 8: 4057 (1980); EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebenlist, et al, *Cell* 20: 269 (1980)).

In addition to prokaryates, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example, (Stinchcomb, et al, *Nature*, 282: 39 (1979); Kingsman, et al, *Gene*, 7: 141 (1979); Tschemper, et al, *Gene*, 10: 157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics*, 85: 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.*, 255: 2073 (1980)) or other glycolytic enzymes (Hess, et al, *J. Adv. Enzyme Reg.*, 7: 149 (1968); Holland, et al, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences. It will be understood that this invention, although described herein in terms of a preferred embodiment, should not be construed as limited to those sequences exemplified.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature*, 273: 113 (1978) incorporated herein by reference). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

B. Methods Employed

If cells without formidable cell wall barriers are used as host cells, transfection is carried out by the calcium phosphate precipitation method as described by Graham and Van der Eb, *Virology*, 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N., et al, *Proc. Natl. Acad. Sci.* (USA), 69: 2110 (1972).

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of *E. coli* DNA Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.*, 8: 4057 (1980), incorporated herein by reference.

For ligation, approximately equimolar amounts of the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

The ligation mixture was used to transform *E. coli* K12 strain 294 (ATLC 31446), and successful transformants were selected by ampicillin resistance. Plasmids from the transformants were prepared, analyzed by restriction and/or sequenced by the method of Messing, et al, *Nucleic Acids Res.*, 9: 309 (1981) or by the method of Maxam, et al, *Methods in Enzymology*, 65: 499 (1980).

C. Preferred Embodiments

The following description of preferred embodiments involving polypeptide expression in *E. coli* is intended to illustrate but not to limit the invention.

C.1 Isolation of cDNA clones coding for mouse pro-βNGF

In order to obtain a gene coding for the β-subunit of human NGF, it was determined to use cloned cDNA coding for mouse βNGF as a hybridization probe.

The cDNA cloning approach took advantage of the known amino acid sequence of the mouse βNGF subunit which is shown in FIG. 1, employing synthetic oligonucleotide primers; the difference in NGF levels found in male and female mouse salivary glands was used as an additional means of identification. Three small portions of the mouse βNGF amino acid sequence were chosen, and oligonucleotide pools complementary to all possible sequences coding for them were synthesized by the method of Crea, et al, *Nucleic Acids Res.*, 8: 2331 (1980). The nucleotide sequences for the coding and complementary strands are shown in FIG. 1.

Initial attempts to identify or isolate mouse βNGF cDNA clones from an oligo dT-primed, cDNA bank from male mouse salivary glands failed, using the synthetic oligonucleotides as hybridization probes. This result indicated that while βNGF comprised 0.1 percent of the protein in the male salivary glands, its mRNA was not of equal abundance. Therefore, the primer pool representing sequences closest to the carboxyl terminus of the protein (FIG. 1, 1) was used to specifically prime reverse transcription of polyA-containing (A+) RNA, from male salivary glands, in order to first enrich for βNGF-specific nucleotide sequences. Molecules of cDNA greater than 200 bp in length were cloned into the well known plasmid pBR322. A total of 10,000 clones was screened using the 5'-$^{32}$P-labeled NGF primer pool originally used in the cDNA priming as a hybridization probe and 0.8 percent of the clones gave a positive signal under high stringency hybridization conditions. It is likely that the remaining 99.2 percent of the "primed" cDNA bank resulted from self-priming as well as from priming by trace amounts of oligo dT eluted during preparation of polyA+ MSG RNA. S1 nuclease treatment during the cloning procedure may also have damaged some of the terminal primer sequence, resulting in fewer detected positive clones.

Clones scored as positive in the first screen were rescreened using radiolabeled primer pools 2 and 3, derived from DNA sequences upstream from oligonucleotide pool 1 as shown in FIG. 1, as hybridization probes. In addition, $^{32}$P-cDNA primed with pool 1 from polyA+ RNA from either male or female mouse salivary glands were used as probes on duplicate filters. A total of 10 male-specific clones, again in pBR322, which hybridized with oligonucleotide pools 2 and 3 was identified. Restriction enzyme analyses demonstrated that all 10 had common HaeIII and HinfI fragments. The clone containing a plasmid which we designated pmβN-9G1 and which expressed the longest DNA insert (~700 bp) was sequenced in its entirety. The amino acid sequence deduced from the nucleotide sequence contained the expected NGF sequence in one translational frame in addition to an NH$_2$-terminal prosequence. See FIG. 4. Further details of the construction and identification of bacterial clones containing mouse NGF cDNA sequences are given hereinafter.

Figure 3:
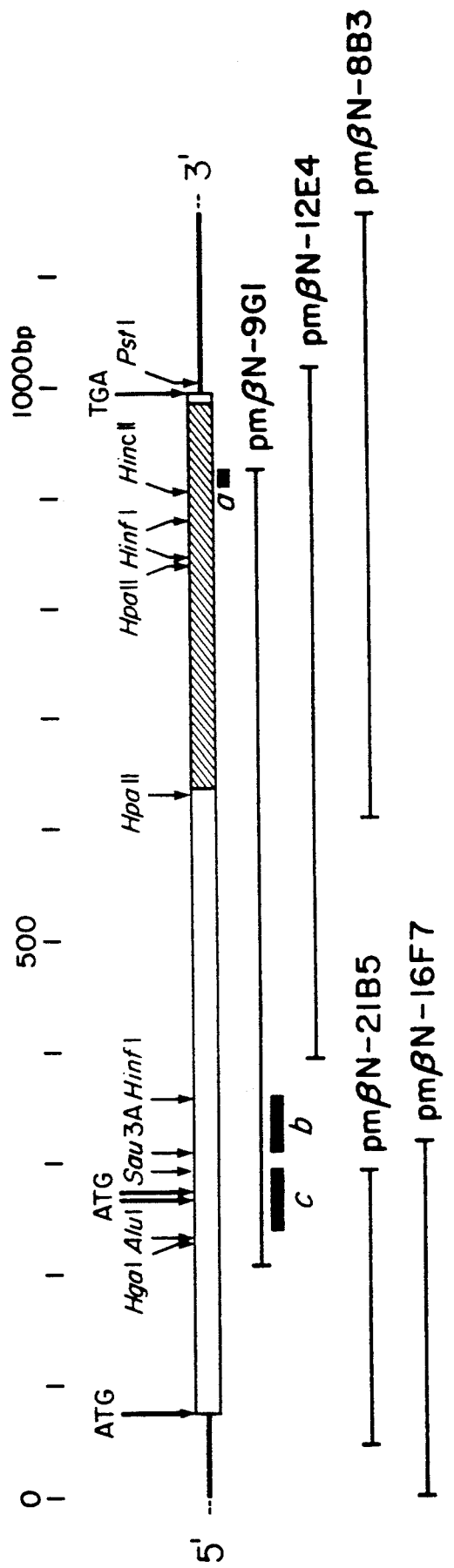
FIG. 3 is a partial restriction map of the mouse NGF gene and the approximate correspondence between the nucleotide sequences of plasmids constructed in the making of the invention with the nucleotide sequence of the mouse NGF gene.

In order to determine the size of the complete NGF mRNA, northern blot hybridization as well as primer extension analysis was employed. A 470 bp long $^{32}$P-labeled DNA fragment (RsaI-RsaI 789, FIG. 3) that included NGF as well as propeptide sequences hybridized to an RNA species about 1300 nucleotides long which was male mouse salivary gland specific. A primer extension experiment using 2 short, double stranded, 5' end-labeled restriction fragments (see legend, FIG. 3) localized the 5' end of the βNGF mRNA to about 230 bases upstream from the 5' end of the pmβN-9G1 cDNA fragment, leaving approximately 370 bases downstream from the 3' end of our clone. All but ~30 nucleotides of the missing 5' sequences are contained in clones we designated pmβN-16F7 and pmβN-21B5, which overlap each other and clone pmβN-9G1 as shown in FIG. 3 and which were isolated as described in the more detailed discussion hereinafter concerning the use of restriction fragments to prime cDNA synthesis.

In order to obtain cloned cDNA which included the sequences from the 3' end of the primer sequence downstream to the 3' polyA sequence, we first enriched for βNGF mRNA by fractionating total polyA+ male mouse salivary gland RNA on a preparative urea agarose gel. The largest size fraction, containing sequences hybridizing to a βNGF cDNA probe, was used for oligo dT-primed cDNA synthesis and cloning. The screening of 3,700 clones resulted in 4 positive hybridization signals. Nucleotide sequence analysis of clones we designated pmβ N-12E4, and pmβN-8B3 added 239 nucleotides to the 3' coding and untranslated sequences. Although oligo dT primed, none of our clones contained the entire 3' untranslated region of βNGF mRNA due to incomplete synthesis of the second DNA strand or to extensive S1 nuclease treatment. Northern blot analysis (FIG. 2) indicated that the polyA sequence was not far beyond the sequences we cloned. Further details of the preparation of oligo dT primed cDNA clones from enriched mRNA are provided hereinafter.

C.2 Isolation and characterization of the human chromosomal βNGF gene

Figure 5A:
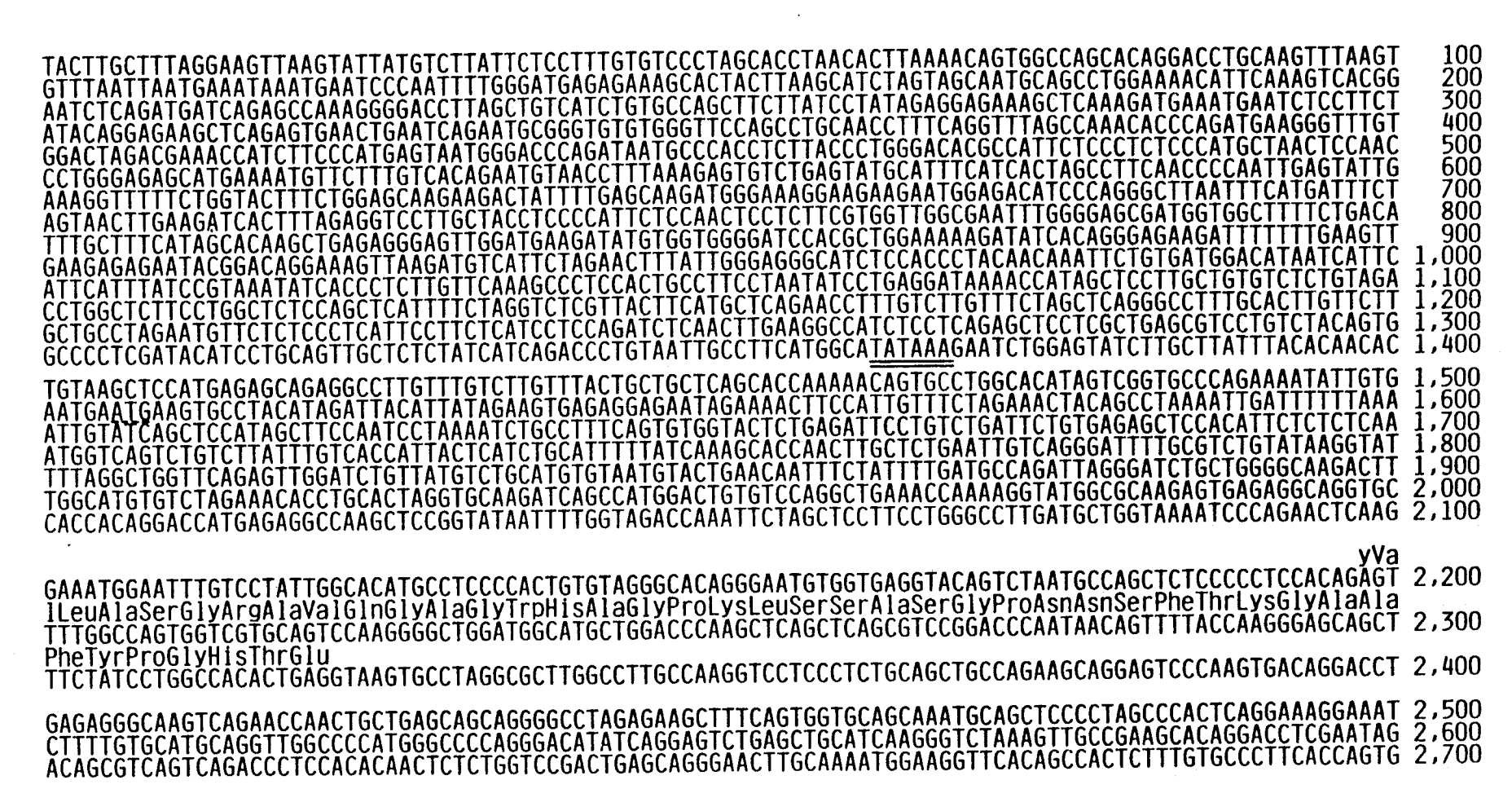
Figure 5B:
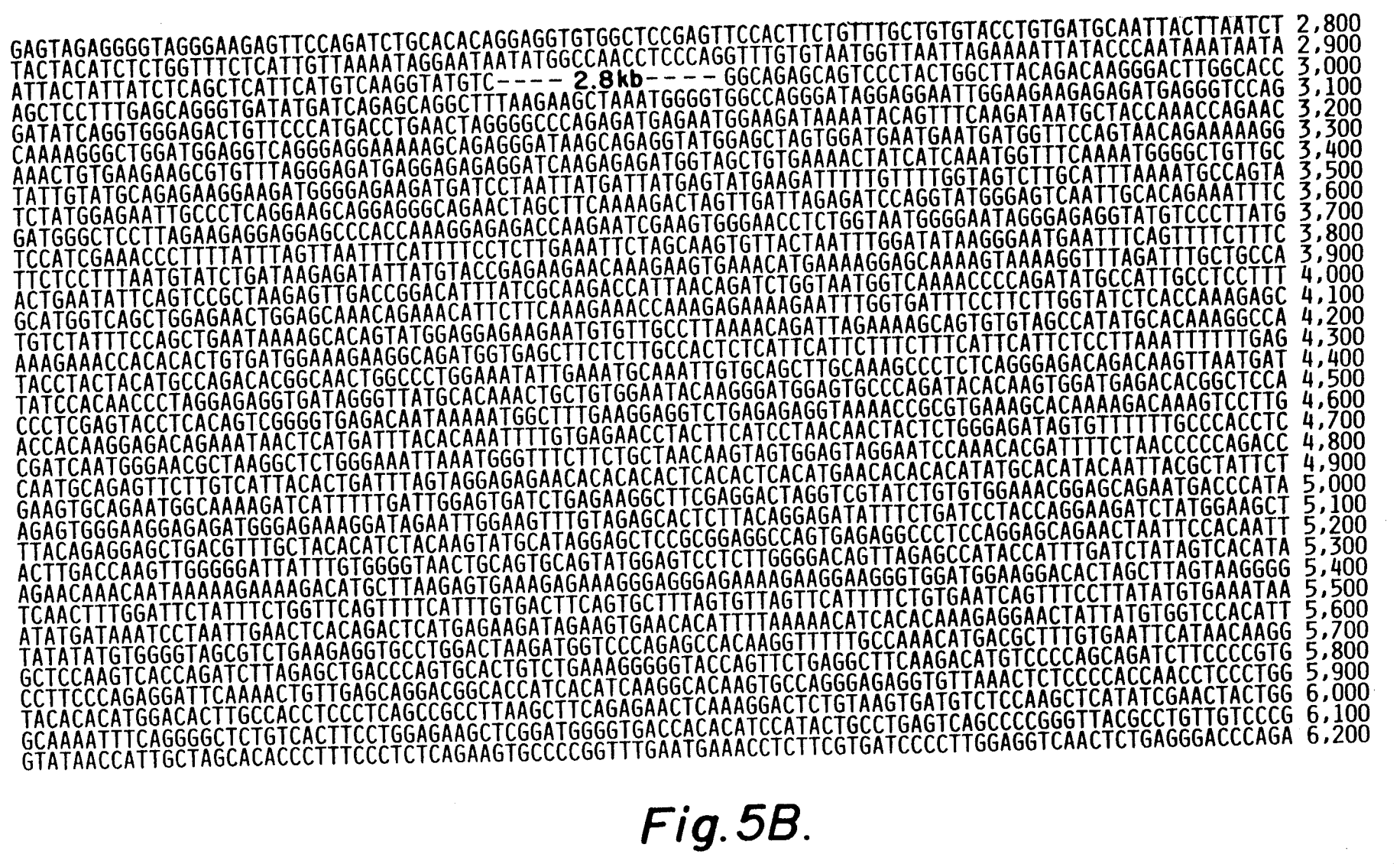
Figure 5C:
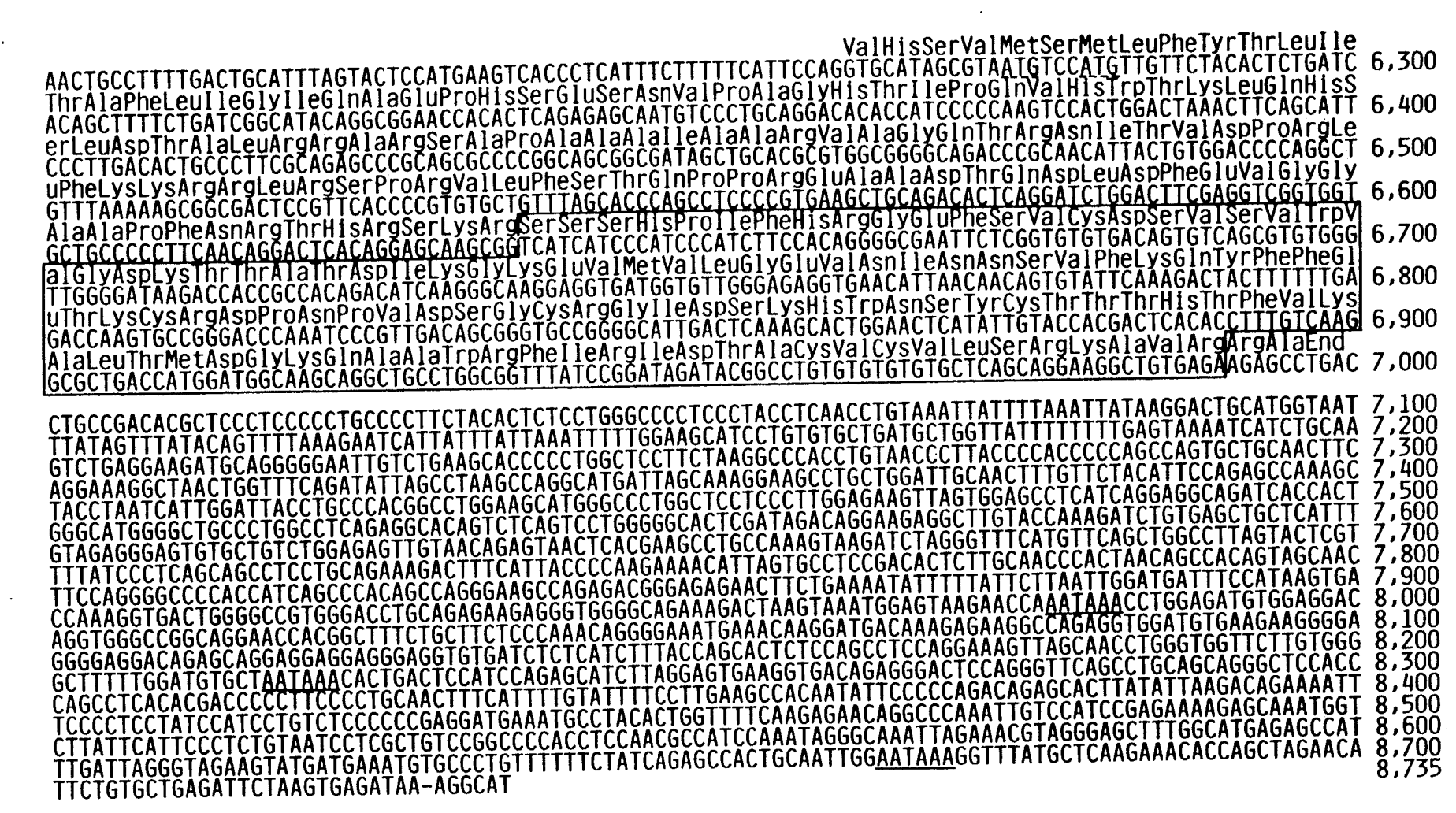

A human gene library (consisting of 15–20 kb, partial HaeIII/AluI human fetal liver DNA fragments inserted into λCharon 4A vectors) was screened using the 470 bp mouse NGF cloned cDNA fragment (pmβN-9G1 RsaI fragment) described above as radioactive hybridization probe. A total of 27 recombinant phage were plaque purified and partially characterized by EcoRI digestion; the 27 phage displayed 6 different types of restriction patterns. Each pattern category shared restriction fragments and thus appeared to overlap the same genomic region. The phage designated γhβN8 was further characterized by physical mapping and nucleotide sequencing; FIG. 4 shows a physical map of clone γhβN8 and regions flanking its sequences in the human genome, generated by phage mapping, sequencing and genomic Southern blotting experiments. A portion of a 12,000 bp nucleotide sequence derived from subcloned, overlapping EcoRI and HindIII fragments is shown in FIG. 5.

C.3 Comparison of the sequences of mouse βNGF cDNA with the human βNGF gene

The mouse βNGF cDNA sequence contains a reading frame with the potential to code for mature βNGF, and the predicted amino acid sequence corresponds to the known sequence of mouse βNGF. Angeletti, et al, *Biochemistry*, 12: 90 (1973) and 12: 100 (1973). Unexpectedly, the cDNA sequence predicts a C-terminal, arginine-glycine dipeptide extension, linked onto the end of the reported sequence for mouse βNGF.

The human βNGF gene contains a region predicting an amino acid sequence approximately 90 percent homologous with the mature mouse βNGF amino acid sequence, which, therefore, must be the gene for human βNGF. The human βNGF protein also has a C-terminal dipeptide extension.

Figure 6B:
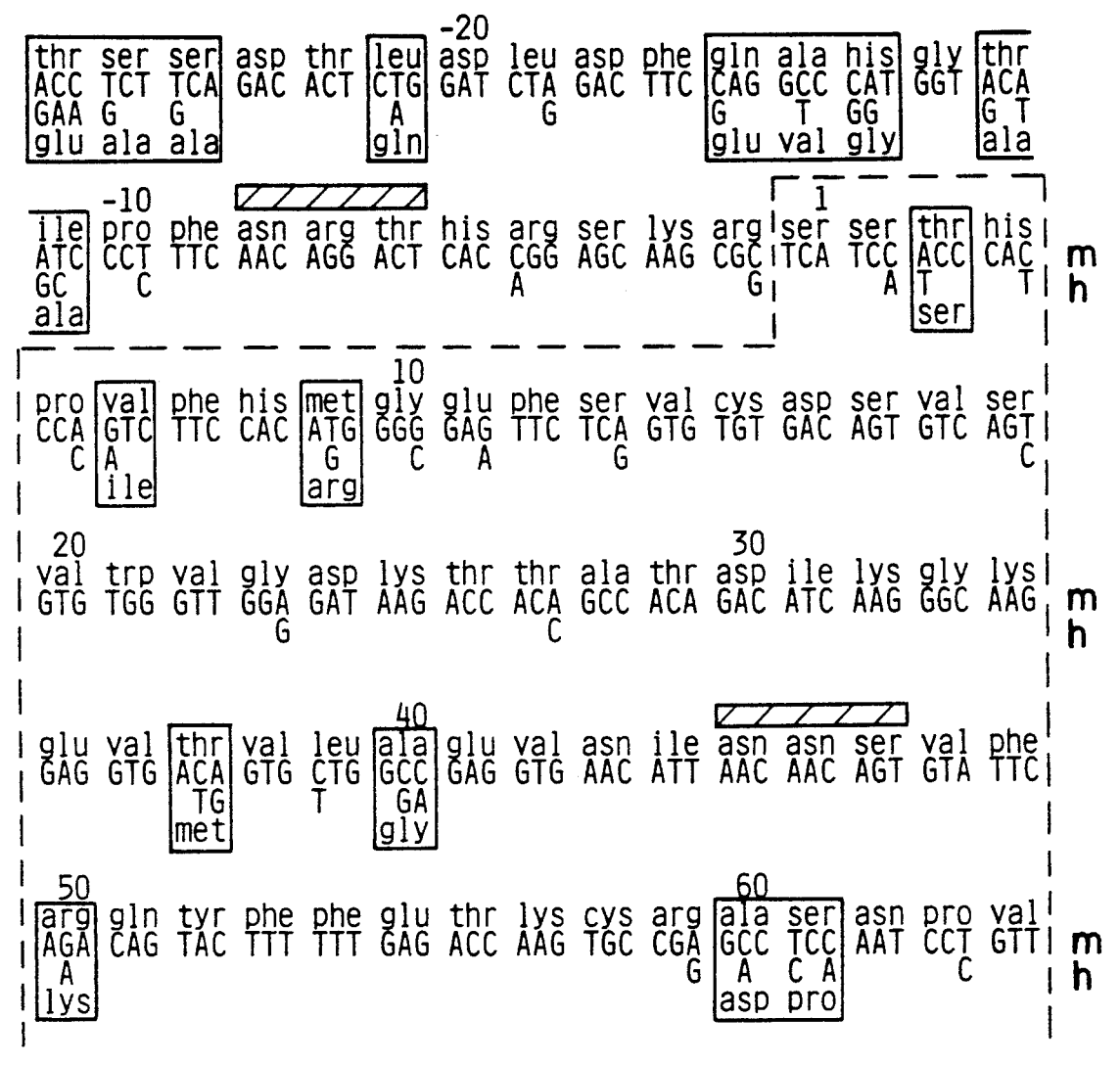

When one aligns the human and mouse βNGF sequences (FIG. 6) it becomes clear that extensive homology extends a significant distance upstream from the known sequence of the mature mouse protein. Evidence has been presented for the existence of a 22,000 dalton biosynthetic pro-βNGF precursor, Berger and Shooter, *Proc. Nat. Acad. Sci. (USA)*, 74: 3647, (1977), which may extend upstream from the mature protein to a potential arginine-arginine cleavage site at nucleotide positions 419 and 420 in FIG. 6. The nucleotide sequence-predicted precursor is longer than that previously detected; as will be described below, the entire prepro-β-NGF sequence is predicted to have a molecular weight of 27,000, the pro-sequence is predicted to be 25,000 daltons, and considering the presence of specific pairs of arginine residues, processing intermediates of 21,500 and 18,000 daltons exist within the cell.

C.4 Localization of the Initiation Methionine Codon and Signal Sequence

Three methionine residues are candidates for designation as the protein synthesis initiation codon (amino acids -187, -121 and -119 in FIG. 6); however several factors strongly implicate amino acid -121 of our sequence as the actual initiation codon employed. Since βNGF is a secreted protein, the initiation codon is likely to be followed by a signal sequence for cotranslational transfer of this polypeptide into the lumen of the endoplasmic reticulum. Amino acids -121 to -104 represent an excellent candidate signal sequence. These 18 amino acids are of the correct length and include a stretch of six completely hydrophobic amino acids (ala-phe-leu-ile-gly-val). Cleavage by signal peptidase could occur between the small amino acid ala-104 and the glu residue at position -103. It is known that signal peptidase cleaves after an identical gln-ala sequence to leave an identical N-terminal glu residue in the case of pre-alpha lactalbumin. The stretch of amino acids following the met residue at position -187 contains a high percentage of polar and charged amino acids and bears no resemblance to any previously described signal sequence.

Therefore, it seems most likely that methionine -121 is used for translation initiation of mouse and human pre-pro-βNGF which would result in a 27,000 dalton pre-prohormone and a 25,000 dalton pro-βNGF if signal peptide processing occurs at residue -104.

C.5 Direct expression of human βNGF in *E. coli*

EcoRI fragments from λhβN8 were subcloned in pBR322. A subclone plasmid we designated phβN8-B9 contained a 2 kb human DNA insert, including most of the sequences coding for the human βNGF subunit. Sequencing determined that only the 10 $NH_2$-terminal amino acids were excluded from this sequence. Our approach for expression of the βNGF coding sequence in *E. coli* was to excise the largest possible fragment from the βNGF coding portion of phβN8-B9, to subsequently fill in missing codons, and to modify the 5' and 3' ends of the sequence to make it suitable for insertion into an *E. coli* expression plasmid. The expression system employed was the Trp promoter system described in U.S. Pat. No. 4,663,283, issued May 5, 1987, and previously used for a variety of genes.

The plasmid phβN8-B9 was digested with EcoRI and HgiAI and a ~300 bp fragment was isolated from the digestion mixture. This fragment is shown in FIG. 7, with the sticky end termini resulting from the two step digestion indicated. In order to construct the 5' end of the human βNGF sequence for expression, the codons for the 10 missing amino acids, the initiator methionine codon (ATG), and nucleotides preceding the ATG which are part of a ribosome binding site and include the cleavage site for the restriction endonuclease XbaI were added; four oligonucleotides were chemically synthesized for this purpose and are shown in FIG. 7 as oligonucleotides I-IV.

The 3' end of the βNGF coding region was modified as follows: the nucleotide sequence of both DNA strands downstream from the single HgiAI site shown in FIG. 7 (at amino acid position Val 111 and Leu 112 of the mature human βNGF) was chemically synthesized, including a termination codon (TAG) following Arg 118 and a SalI sticky end. These oligonucleotides are fragments V and VI in FIG. 7.

Synthetic oligonucleotides I-VI were radioactively labeled with T4 polynucleotide kinase and $\gamma$-$^{32}$P-ATP, and the radioactive oligonucleotides were mixed with the ~300 bp hβNGF DNA fragment in T4 DNA ligase buffer. Ligation was carried out with 10 units of T4 DNA ligase a 12° C. for 12 hrs. The mixture was phenol extracted and the DNA was precipitated in 70 percent ethanol. The precipitate was dried, dissolved in restriction endonuclease buffer, and the enzymes XbaI and SalI were added. Digestion was carried out for 2 hrs.

Preparative gel electrophoresis of the DNA mixture and autoradiography demonstrated the presence of a radioactive doublet at ~370 bp. The bands were cut out separately and electrophoretically eluted. The eluted DNA fragments were then ligated (T4 DNA ligase) to a HGH-Trp expression plasmid designated pHGH207-1 that had been treated with bacterial alkaline phosphatase after digestion with XbaI and SalI. (The alkaline phosphatase treatment was used to prevent reinsertion of the HGH fragment into the Trp expression vector.) The ligation mixture was used to transform *E. coli* K12/294 (ATCC 31446). Ampicillin resistant and tetracycline sensitive colonies were selected on agar plates; two hundred colonies were screened for the presence of human βNGF sequences by hybridization with a radioactive 300 bp EcoRI/HgiAI probe. Twelve positive colonies were analyzed for the presence of immunoreactive βNGF molecules in their cell extracts using rabbit anti-mouse βNGF antibodies on a Western blot. All but one clone showed a positive signal of the expected molecular weight, compared with a negative control extract. DNA sequence analysis of one of the clones verified, that the final plasmid, designated by us as phβNGFtrpl, which resulted in human βNGF expression had the originally planned construction.

Figure 8:
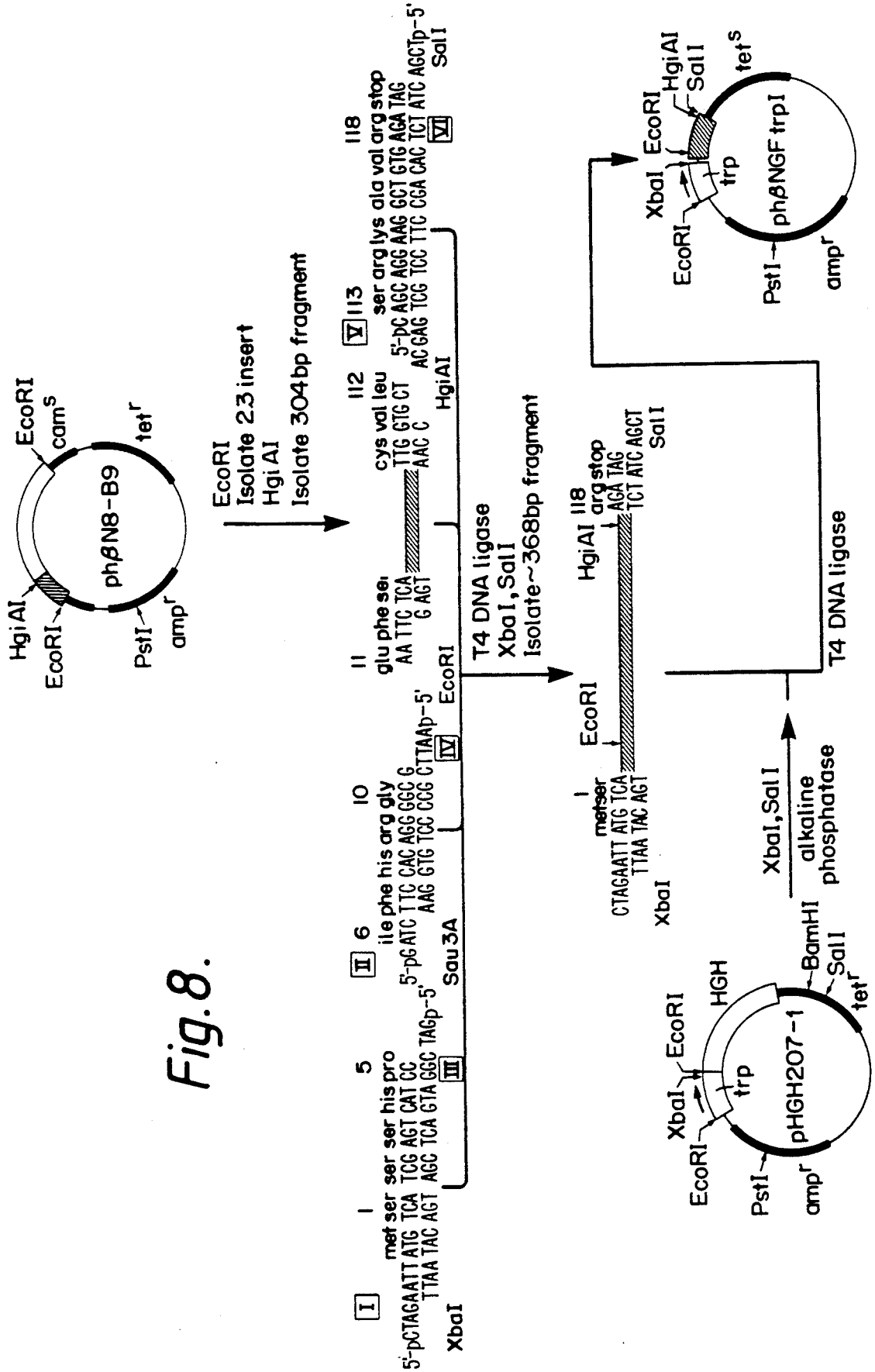
FIG. 8 depicts a portion of the process for assembling the plasmid phβNGFtrpl for transformation of *E. coli* to express human βNGF.

The sequence of operations from digestion of plasmid phβN8-B9 with EcoRI and HgiAI to assembly of plasmid phβNGFtrpl is shown in FIG. 8. The plasmid pHGH207-1 was obtained (H. de Boar, et al., op cit.) from plasmid pHGH207, U.S. Pat. No. 4,663,283, by digestion with BamHI followed by partial digestion with EcoRI. The largest fragment which contained the trp promoter was isolated. The largest EcoRI-BamHI fragment from pBR322 was also isolated and the two fragments were ligated and used to transform E. coli K12/194 (ATCC 31446). Clones resistant to both ampicillin and tetracycline contained pHGH207-1.

C.6 Construction and identification of bacterial clones containing mNGF cDNA sequences Two pools of 8 primers each (14 bases) were chemically synthesized. Each primer was complementary to a potential mRNA sequence for amino acids 93-96 and a portion of 97. A mixture of the 16 oligonucleotides was used to specifically prime the synthesis of cDNA on poly(A+)RNA. 220 pmoles (1 µg) of each pool of 8 primers (440 pmoles total, 2 µg) were annealed with 40 µg poly(A+) RNA in 50 µl of 100 mmole KCl by incubating for 4 minutes each at 90° C., 68° C., 42° C., and 37° C. $^{32}$P-labeled cDNA was synthesized in a 100 µl reaction in 50 mM Tris pH 8.3, 10 MM MgCl$_2$, 10 mM DTT, 50 mM KCl. The reaction contained, in addition to annealed mixture, 500 µM dATP, TTP, dGTP, 100 µM dCTP, 20 µCi [α-$^{32}$P] dCTP (2000 Ci/mmole, Amersham), 0.5 units/µl RNAsin, and 90 units reverse transcriptase. First strand synthesis was for 60 minutes at 37° C. The reaction was boiled for 3 minutes, quenched on ice for 1 minute, and spun in a microfuge. The supernatant was diluted with an equal volume ddH$_2$O and ds cDNA was synthesized with the addition of 15 units of Klenow PolI for 18 hours at 12° C. After phenol-chloroform extraction and ethanol-precipitation, the preparation was digested with $10^3$ units of S1 nuclease in 150 µl for 1 hr at 37° C. After phenol-chloroform extraction and ethanol-precipitation the cDNA was fractionated by electrophoresis on a 5 percent polyacrylamide gel. Two size ranges of cDNA were electroeluted. 132 ngm were recovered ~550 bp (upper) in length and 182 ngm were recovered 200-550 bp (lower) in length. A total of 20 ngm of each fraction was extended at the 3'-termini with 20-40 d(C) residues using terminal nucleotidyl transferase. The d(C)-tailed cDNA was annealed with 150 ngm of pBR322 which had been similarly extended with d(G) residues at the PstI site. Annealings were in 50 µl 100 mM NaCl, 10 mM Tris pH 7.5, 250 mM EDTA. Mixtures were heated to 70° C., allowed to cool slowly to 37° C. (16 hrs), then to 4° C. (6 hrs). One-half of the annealed mixture was used to transform E. coli K-12 strain 294. 500 colonies from each size fraction (upper and lower) were screened by filter hybridization. $^{32}$P-labeled probe was prepared from a mixture of the 16 primers (1 µg total) by phosphorylation with 200 µCi [α-$^{32}$P] ATP (5000 Ci/mmole, Amersham) and polynucleotide kinase (P-L Biochemicals) by a published procedure. The filters containing the 10,000 clones were hybridized with ~1×10$^8$ cpm of the $^{32}$P-labeled probe at room temperature for 18 hours in a primer hybridization mix (100 mM Tris pH 7.5, 0.9M NaCl, 6 mM EDTA, 1× Denhardt's solution, 100 µM rATP, 1 mM NaH$_2$PO$_4$-Na pyrophosphate, 0.5 percent Nonidet P-40, 0.1 mg/ml yeast RNA (Sigma R-6750)). Filters were washed 30 minutes (3 times) in 6× SSC at 42° C. and exposed to X-ray film for 16 hrs at −70° C. with an intensifying screen (Dupont). Approximately 0.7-0.9 percent (370 upper, 460 lower) of the colonies were selected for a second round of screening with 2 additional synthetic primers which are 5' to the original priming site. 12-mers complementary to all potential mRNA sequences for amino acids 74-77 were synthesized in 2 pools of 4 primers each. Two pools of 8 14-mers each were similarly synthesized, complementary to potential mRNA sequences for amino acids 52-58 and a portion of 56. Three sets of identical filters were prepared from the "upper" and "lower" colonies selected in the first round of screening. $^{32}$P-labeled probes were prepared as before from the 4 synthetic oligonucleotides. Filters were hybridized with 0.5×10$^8$ cpm in primer hybridization mix, washed, and exposed to X-ray film. There were nine positives (3 from "lower", 6 from "upper") which hybridized with all of the 5' oligonucleotides. Plasmid DNA was isolated by a miniscreen procedure and the clone with the largest insert determined by restriction analysis. The plasmid designated pmβN-9G1 was completely sequenced by the Maxam-Gilbert method. The cDNA insert contained the 14 base primer sequence (FIG. 1, pool 1) and a total of 716 bp.

C.7 Oligo dT-primed cDNA clones prepared from mRNA enriched for βNGF message 200 µg of poly(A+) RNA was fractionated by electrophoresis through a denaturing agarose gel composed of 2 percent agarose in 0.025M sodium citrate pH 3.8 and 6M urea. The ribosomal bands were visualized by staining a thin vertical slice with ethidium bromide. The gel was cut into 0.5 cm slices, melted at 70° C., extracted vigorously twice with phenol and once with chloroform. After 2 ethanol precipitations the pellet was dissolved in 30 µl ddH$_2$O. 1 µl aliquots of each fraction (in 5 µl 4M ammonium acetate pH 7.0) were spotted onto a dry nitrocellulose filter and screened by dot hybridization under stringent conditions. A $^{32}$P-labeled probe was prepared from the pmβN-9G1 insert by a published procedure utilizing calf thymus DNA fragments as primers in a Klenow Pol 1 reaction. The filter was hybridized with ~10$^7$ cpm in 50 mM NaPO$_4$ pH 7.0, 5× Denhardt's solution, 5× SSC, 50 µg/ml sonicated herring sperm DNA, 100 µM rATP, 1 mM NaH$_2$PO$_4$-sodium pyrophosphate, and 50 percent formamide at 42° C. for 18 hrs. The filter was washed 20 minutes (3 times) in 0.2× SSC-0.1 percent SDS at 42° C. and exposed to film. Hybridization results localized the NGF message to fractions 11 and 12. Oligo-dT-primed cDNA was prepared by standard methods using 10 µl each of fractions 11 and 12. The cDNA longer than 600 bp was eluted from gel slices after electrophoresis on a 5 percent polyacrylamide gel. Approximately 40 ngm cDNA from fraction 11 and 20 ngm from fraction 12 were d(C)-tailed and annealed with d(G)-tailed pBR322. About 3300 clones from fraction 11 and 1500 clones from fraction 12 were screened as colonies by filter hybridization under stringent conditions using a $^{32}$P-labeled internal HpaII fragment (216 bp) from pmβN-9G1. Filters were hybridized with 50×10$^6$ cpm at 42° C. for 18 hrs, washed, and exposed to X-ray film as before. Five clones from fraction 12 were "positive" with this probe. Restriction analyses showed they were siblings. pmβN-12E4 was completely sequenced by the Maxam-Gilbert method. Two clones from fraction 11 were "positive". The largest, pmβN-8B3, was completely sequenced by Maxam-Gilbert method.

C.8 Pharmaceutical Compositions

The human β-NGF of the present invention can be formulated according to known methods to prepare pharmaceutically useful compositions whereby the β-NGF is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective parenteral administration to the host.

The human β-NGF hereof may be parenterally administered to subjects suffering from nerve damage or other conditions for which it is therapeutically effective. Dosage and dose rate may parallel that currently in use in clinical investigations of such agents derived, for example, from mouse salivary glands.

Notwithstanding that reference has been made to particular preferred embodiments, it will be further understood that the present invention is not to be construed as limited to such, rather to the lawful scope of the appended claims.

We claim:

1. A process which comprises transforming a host cell with a replicable expression vector capable, in the host cell transformed with the vector, of expressing an isolated first DNA sequence which encodes a polypeptide comprising the human mature βNGF amino acid sequence

```
ser ser ser his pro ile phe his arg gly glu phe ser val cys
asp ser val ser val trp val gly asp lys thr thr ala thr asp
ile lys gly lys glu val met val leu gly glu val asn ile asn
asn ser val phe lys gln tyr phe phe glu thr lys cys arg asp
pro asn pro val asp ser gly cys arg gly ile asp ser lys his
trp asn ser tyr cys thr thr thr his thr phe val lys ala leu
thr met asp gly lys gln ala ala trp arg phe ile arg ile asp
thr ala cys val cys val leu ser arg lys ala val arg
``` operably linked with a second DNA sequence capable of effecting expression of the first DNA sequence in the host cell transformed with the operably linked DNA sequences.

2. A process according to claim 1 wherein the host cell is prokaryotic.
3. A process according to claim 1 wherein the host cell is eukaryotic.
4. A process according to claim 1 wherein the host cell is a yeast cell.
5. A process according to claim 1 wherein the host cell is a mammalian cell.
6. A process according to claim 1 wherein the host cell is a Chinese hamster ovary cell.
7. A process according to claim 1 which further comprises culturing the transformed host cell and recovering the expressed human mature βNGF from the cell culture.
8. A method of using a host cell transformed with a replicable expression vector capable of expressing an isolated DNA sequence encoding the human mature βNGF amino acid sequence

```
ser ser ser his pro ile phe his arg gly glu phe ser val cys
asp ser val ser val trp val gly asp lys thr thr ala thr asp
ile lys gly lys glu val met val leu gly glu val asn ile asn
asn ser val phe lys gln tyr phe phe glu thr lys cys arg asp
pro asn pro val asp ser gly cys arg gly ile asp ser lys his
trp asn ser tyr cys thr thr thr his thr phe val lys ala leu
thr met asp gly lys gln ala ala trp arg phe ile arg ile asp
thr ala cys val cys val leu ser arg lys ala val arg
``` which comprises culturing the host cell under conditions such that the expression vector is replicated.

9. A method of using a host cell transformed with a replicable expression vector capable of expressing an isolated DNA sequence encoding the human mature βNGF amino acid sequence

```
ser ser ser his pro ile phe his arg gly glu phe ser val cys
asp ser val ser val trp val gly asp lys thr thr ala thr asp
ile lys gly lys glu val met val leu gly glu val asn ile asn
asn ser val phe lys gln tyr phe phe glu thr lys cys arg asp
pro asn pro val asp ser gly cys arg gly ile asp ser lys his
trp asn ser tyr cys thr thr thr his thr phe val lys ala leu
thr met asp gly lys gln ala ala trp arg phe ile arg ile asp
thr ala cys val cys val leu ser arg lys ala val arg
``` which comprises culturing the host cell under conditions such that human mature βNGF accumulates in the culture.

* * * * *